United States Patent [19]
Davenport

[11] Patent Number: 5,666,945
[45] Date of Patent: Sep. 16, 1997

[54] PNEUMATICALLY-OPERATED GAS DEMAND APPARATUS

[75] Inventor: James M. Davenport, Fallbrook, Calif.

[73] Assignee: Salter Labs, Arvin, Calif.

[21] Appl. No.: 488,202

[22] Filed: Jun. 7, 1995

[51] Int. Cl.$^6$ .................................................. A61M 11/00
[52] U.S. Cl. .................... 128/200.14; 128/204.23; 128/204.26; 128/207.18
[58] Field of Search ................ 128/204.26, 204.23, 128/205.24, 200.14, 203.12, 207.18

[56] References Cited

U.S. PATENT DOCUMENTS

| | | | |
|---|---|---|---|
| 2,414,747 | 1/1947 | Kirschbaum | 128/142 |
| 2,535,844 | 12/1950 | Emerson | 128/195 |
| 3,530,856 | 9/1970 | Bird et al. | 128/145.6 |
| 3,537,448 | 11/1970 | Liston | 128/14.5 |
| 3,896,800 | 7/1975 | Cibulka | 128/145.8 |
| 4,054,133 | 10/1977 | Myers | 128/142.2 |
| 4,057,059 | 11/1977 | Reid, Jr. et al. | 128/145.8 |
| 4,106,503 | 8/1978 | Rosenthal et al. | 128/204.26 |
| 4,163,450 | 8/1979 | Kirk et al. | 128/145.8 |
| 4,240,419 | 12/1980 | Furlong et al. | 128/204.23 |
| 4,498,471 | 2/1985 | Kranz et al. | 128/204.26 |
| 4,575,042 | 3/1986 | Grimland et al. | 251/46 |
| 4,686,974 | 8/1987 | Sato et al. | 128/204.23 |
| 5,074,298 | 12/1991 | Arnoth | 128/204.18 |
| 5,137,017 | 8/1992 | Salter | 128/207.18 |
| 5,165,397 | 11/1992 | Arp | 128/204.21 |
| 5,241,955 | 9/1993 | Dearman et al. | 128/204.18 |
| 5,251,618 | 10/1993 | Christianson | 128/205.24 |
| 5,265,596 | 11/1993 | Sauze | 128/205.24 |
| 5,275,153 | 1/1994 | Kay | 128/205.24 |
| 5,280,780 | 1/1994 | Abel | 128/203.14 |
| 5,343,858 | 9/1994 | Winefordner et al. | 128/204.26 |
| 5,360,000 | 11/1994 | Carter | 128/204.26 |

FOREIGN PATENT DOCUMENTS

WO 84/01293  4/1994  WIPO.

OTHER PUBLICATIONS

Auerbach, David, D.V.M., M.D. et al., "A New Oxygen Cannula System Using Intermittent-Demand Nasal Flow", *Chest*, 74:1, Jul., 1978, pp. 39–44.

*Primary Examiner*—Aaron J. Lewis
*Attorney, Agent, or Firm*—Shoemaker and Mattare, Ltd.

[57] ABSTRACT

A pneumatically-operated gas demand apparatus coupled in interruptible fluid communication between a recipient and a first source of a pressurized first gas controls delivery of the first gas to the recipient as the recipient inhales and exhales and comprises a supply valve and a sensing valve. The supply valve has a first interior chamber divided by a flexible first diaphragm into a supply chamber region and a control chamber region. The supply chamber region is in interruptible fluid communication between the first source of the first gas and the recipient. The control chamber region is in continuous fluid communication with a second source of a pressurized second gas. The sensing valve has a second interior chamber divided by a flexible second diaphragm into a venting chamber region and a sensing chamber region. The venting chamber region is in interruptible fluid communication between the control chamber region and an ambient air environment. The sensing chamber region is in continuous fluid communication with the recipient. When the recipient inhales, the second diaphragm moves to a flow-causing position to cause the second gas to flow into the ambient air environment and causes the first diaphragm to move to a flow-supplying position thereby delivering the first gas to the recipient. When the recipient exhales, the second diaphragm moves to a flow-stopping position to prevent the second gas to flow into the ambient air environment and causes the first diaphragm to move to a flow-blocking position thereby preventing delivery of the first gas to the recipient.

13 Claims, 9 Drawing Sheets

— — — INHALATION & EXHALATION PRESSURE
——— GAS FLOW

5,666,945

PNEUMATICALLY-OPERATED GAS DEMAND APPARATUS

FIELD OF THE INVENTION

The present invention relates to a pneumatically-operated gas demand apparatus coupled in interruptible fluid communication between a recipient and a first source of a pressurized first gas and adapted for controlling delivery of the first gas to the recipient as the recipient inhales and exhales. More particularly, the present invention relates to a pneumatically-operated gas demand apparatus coupled in interruptible fluid communication between a recipient/patient and a source of pressurized oxygen or other gas and adapted to deliver that gas to the recipient/patient when the recipient/patient inhales. The present invention can deliver and operate with a single gas such as oxygen or it can deliver one gas such as oxygen and operate with another gas such as compressed air to reduce waste of costly oxygen. The present invention also delivers a high-flow pulse of gas upon initiation of the patient's inhalation phase of the breathing cycle, and can therefore be used to power a nebulizer containing medication through a breathing circuit to a patient.

BACKGROUND OF THE INVENTION

Many medical patients suffering from any one of a variety of lung ailments are often prescribed supplemental oxygen therapy so that the patient could breath oxygen-enriched air throughout the day and sometimes throughout the night. Earlier supplemental oxygen therapy employed a nasal cannula system operably connected between a tank of compressed oxygen and the patient's nose. Oxygen was continuously delivered to the patient throughout the patient's entire breathing cycle. This method of continuously delivering oxygen to the patient throughout the patient's breathing cycle was considered wasteful because much of the oxygen dissipated into the ambient air environment. Better methods of delivering oxygen to the patient were later developed which included improved equipment that would only deliver oxygen to the patient during the inhalation phase of the patient's breathing cycle. Usually, this improved equipment employed a demand valve which opened to deliver supplemental oxygen to the patient only when the patient inhaled. Numerous types of demand valves are well known in the prior art.

One such demand valve is described in U.S. Pat. No. 5,360,000 to Carter. This demand valve is compact, simplified and totally pneumatic. The demand valve which is coupled between a source of pressurized gas such as oxygen and the patient includes a valve body having a gas flow passageway and pneumatically-coupled sensing and slave diaphragms. The slave diaphragm is interposed in the gas flow passageway and prevents gas from flowing during the exhalation phase of the patient's respiratory cycle. During inhalation, which is sensed by a sensing diaphragm, the slave diaphragm moves to open the gas flow passageway, thus permitting flow of gas to the patient. Although effective in delivering gas to a patient upon demand, this demand valve has an inherent problem. When the patient inhales to cause delivery of oxygen to patient, oxygen is also vented into the ambient air environment for as long as the slave diaphragm remains opened. This leads to wastage of oxygen which is the very problem that demand valves were designed to prevent.

Furthermore, this demand valve has an inherent deficiency of delivering gas to the patient in a continuous flow stream upon and during the inhalation phase. Unfortunately, the air remaining in the patient's respiratory passageway i.e. the nasal cavity and the throat, is first taken into the lungs upon inhalation. The oxygen-enriched air then follows the remaining air and only approximately one-half of the oxygen-enriched air ever reaches the lungs. The remaining one-half of the oxygen-enriched air remains in the patient's respiratory passageway during the waning moments of inhalation and is the first to be exhaled therefrom during exhalation. It would be beneficial to the patient if this air remaining in the patient's respiratory passageway after exhalation could be purged or otherwise enriched with oxygen before it is inhaled. Such an approach is utilized in U.S. Pat. No. 4,686,974 to Sato et al.

There is a need in the industry to provide a pneumatically-operated gas demand apparatus which can control delivery of oxygen to the recipient/patient as the recipient inhales and exhales while minimizing wastage of oxygen. It would be advantageous of this pneumatically-operated gas demand apparatus can deliver a high-flow pulse of oxygen to the recipient/patient upon commencement of the inhalation phase of the patient's breathing cycle. Such a high-flow pulse of oxygen delivered upon commencement of the inhalation phase would enrich the air remaining in the patient's respiratory passageway upon inhalation and, simultaneously therewith, purge some of this air therefrom before being inhaled. It would also be advantageous if this pneumatically-operated gas demand apparatus can deliver a continuous flow of oxygen immediately after delivery of the pulse of high-flow oxygen and throughout the remaining portion of inhalation. The present invention satisfies this need and provides these advantages.

OBJECTS AND SUMMARY OF THE INVENTION

An object of the present invention is to provide a pneumatically-operated gas demand apparatus for coupling in interruptible fluid communication between a recipient/patient and a source of pressurized oxygen which can control delivery of oxygen to the recipient/patient as the recipient inhales and exhales while minimizing wastage of oxygen.

Another object of the present invention is to provide a pneumatically-operated gas demand apparatus which can deliver a high-pressure bolus of oxygen to the recipient/patient upon commencement of the inhalation phase of the recipient/patient's breathing cycle and a continuous flow of oxygen thereafter and throughout the remaining period of negative pressure defining the inhalation phase of the breathing cycle.

Yet another object of the present invention is to provide a pneumatically-operated gas demand apparatus which is simple in design and compact.

A still further object of the present invention is to provide a pneumatically-operated gas demand apparatus which can be fabricated from readily available components or can be integrated into a unitary construction.

Accordingly, a pneumatically-operated gas demand apparatus of the present invention is hereinafter described. The pneumatically-operated gas demand apparatus is coupled in interruptible fluid communication between a recipient (or patient) and a first source of a pressurized first gas and is adapted for controlling delivery of the first gas to the recipient as the recipient inhales and exhales. In its broadest form, the pneumatically-operated gas demand apparatus includes a supply valve and a sensing valve. The supply valve includes a supply valve housing and a flexible first diaphragm member. The supply valve housing defines a first interior chamber formed therein. The first diaphragm member is disposed within the first interior chamber and is connected to the supply valve housing in a manner to divide the first interior chamber into a supply chamber region and a control chamber region. The supply chamber region is in interruptible fluid communication with and between the first source of the first gas and the recipient and the control chamber region is in continuous fluid communication with a second source of a pressurized second gas. The first diaphragm member is operative to hermetically seal the supply chamber region and the control chamber region from one another and is operative to move between a flow-blocking position and a flow-supplying position.

The sensing valve includes a sensing valve housing and a flexible second diaphragm member. The sensing valve housing defines a second interior chamber formed therein. The second diaphragm member is disposed within the second interior chamber and is connected to the sensing valve housing in a manner to divide the second interior chamber into a venting chamber region and a sensing chamber region. The venting chamber region is in interruptible fluid communication with and between the control chamber region of the first interior chamber of the supply valve and an ambient air environment and the sensing chamber region is in continuous fluid communication with the recipient. The second diaphragm member is operative to hermetically seal the venting chamber region and the sensing chamber region from one another and is responsive, when the recipient inhales and exhales, to move between a flow-stopping position and a flow-causing position. When the recipient inhales, the second diaphragm member is in the flow-causing position thereby causing the second gas to flow from the control chamber region, through the venting chamber region and into the ambient air environment which, in turn, causes the first diaphragm member to be in the flow-supplying position thereby delivering the first gas from the first source of pressurized first gas to the recipient. When the recipient exhales, the second diaphragm member is in the flow-stopping position thereby preventing the second gas to flow from the control chamber region, through the venting chamber region and into the ambient air environment which, in turn, causes the first diaphragm member to be in the flow-blocking position thereby preventing delivery of the first gas to the recipient.

The pneumatically-operated gas demand apparatus includes a regulator mechanism disposed between and in interruptible fluid communication with the first source of the first gas and the supply chamber region of the supply valve. The regulator mechanism which can be adjusted comprises a regulator housing, a flexible regulator diaphragm and a valve assembly. The regulator housing defines a regulator chamber therein. The regulator diaphragm is disposed within the regulator chamber and is connected to the regulator housing in a manner to divide the regulator chamber into a vented regulator chamber region which is in continuous fluid communication with the ambient air environment and a supply regulator chamber region which is in interruptible fluid communication between the first source of pressurized first gas and the supply chamber region of the supply valve. The regulator diaphragm is operative to hermetically seal the vented regulator chamber region and the supply regulator chamber region from one another.

The valve assembly is operably connected to the regulator diaphragm and is disposed within the supply regulator chamber region. The valve assembly is operative between a closed condition and an opened condition. In the closed condition, an upstream portion of the supply regulator chamber region is in fluid isolation with a downstream portion of the supply regulator chamber region. In the opened condition, the upstream portion of the supply regulator chamber region is in fluid communication with the downstream portion of the supply regulator chamber region. The valve assembly is resiliently and yieldably biased against the regulator diaphragm in the closed condition and the regulator diaphragm is resiliently and yieldably biased against the valve assembly in the opened condition. When a first gas pressure of the first gas reaches a threshold gas pressure amount in the downstream portion of the supply regulator chamber region, the valve assembly is in the closed condition. When the first gas pressure is less than the threshold gas pressure amount, the valve assembly is in the opened condition.

The pneumatically-operated gas demand apparatus also includes a bolus chamber structure, a supply orifice element and a pilot orifice element. The bolus chamber defining a bolus chamber therein is disposed between and in fluid communication with the regulator mechanism and the supply chamber region of the supply valve. The supply orifice element having a supply orifice formed therethrough is disposed between the regulator mechanism and the bolus chamber structure. The pilot orifice element having a pilot orifice extending therethrough is disposed between the second source of pressurized second gas and the control chamber region of the supply valve. The supply orifice and the pilot orifice can be either fixed in size or an adjustably variable in size.

Preferably, the first gas and the second gas are oxygen and, therefore, the first gas and the second gas are the same. With the first and second gases being the same, the first source and second source of pressurized gas could also, but not necessarily, be the same. The first gas and the second gas can be different from each other. If so, the first source and the second source must also be different from one another. The first gas and the second gas are selected from either different ones or the same one of a group of gases consisting of oxygen, nitrous oxide, air and other types of gases.

These and other objects of the present invention will become more readily appreciated and understood from consideration of the following detailed description of the exemplary embodiments of the present invention when taken in conjunction with the accompanying drawings, in which:

DETAILED DESCRIPTION OF THE EXEMPLARY EMBODIMENTS

A pneumatically-operated gas demand apparatus is coupled in interruptible fluid communication between a recipient and a source of pressurized oxygen and is adapted for controlling delivery of oxygen to the recipient as the recipient inhales and exhales. Although the pneumatically-operated gas demand apparatus is specifically suited to provide oxygen to a recipient/patient, one of ordinary skill in the art would appreciate that the present invention can also be adapted and used to deliver other kinds of gases to recipients such as nitrous oxide. Further, since the pneumatically-operated gas demand apparatus can deliver and operate with either a single gas such as oxygen or two gases such as oxygen and inexpensive compressed air, other types of gases can also be employed without departing from the spirit and concepts of the present invention.

Figure 1:
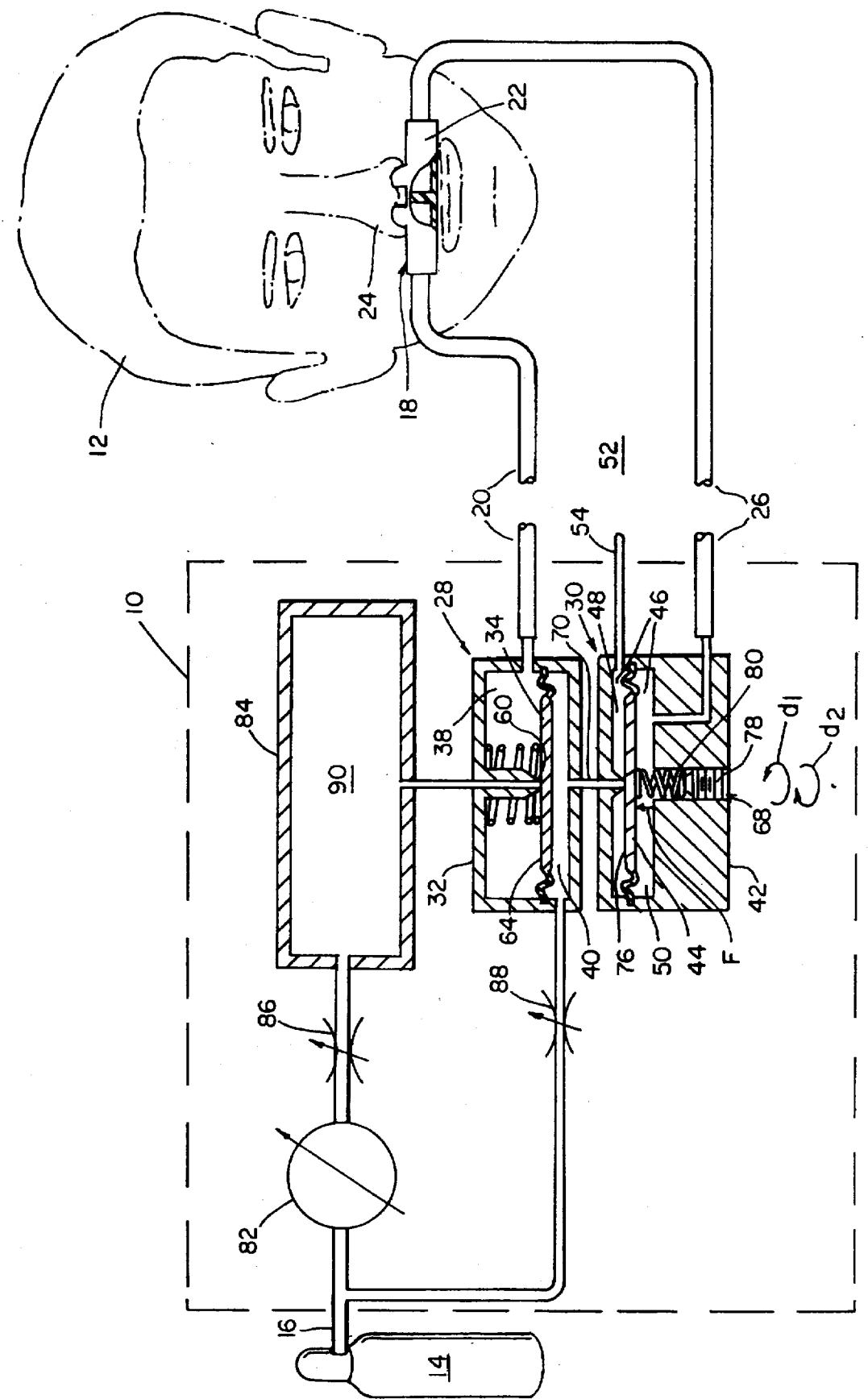
FIG. 1 is partially a schematic view and partially an elevational side view in cross-section of a first exemplary embodiment of a pneumatically-operated gas demand apparatus of the present invention shown coupled between and in fluid communication with a single source of pressurized gas and a recipient with a supply valve in a flow-blocking position and a sensing valve in a flow-stopping position as a result of the recipient exhaling.
Figure 2:
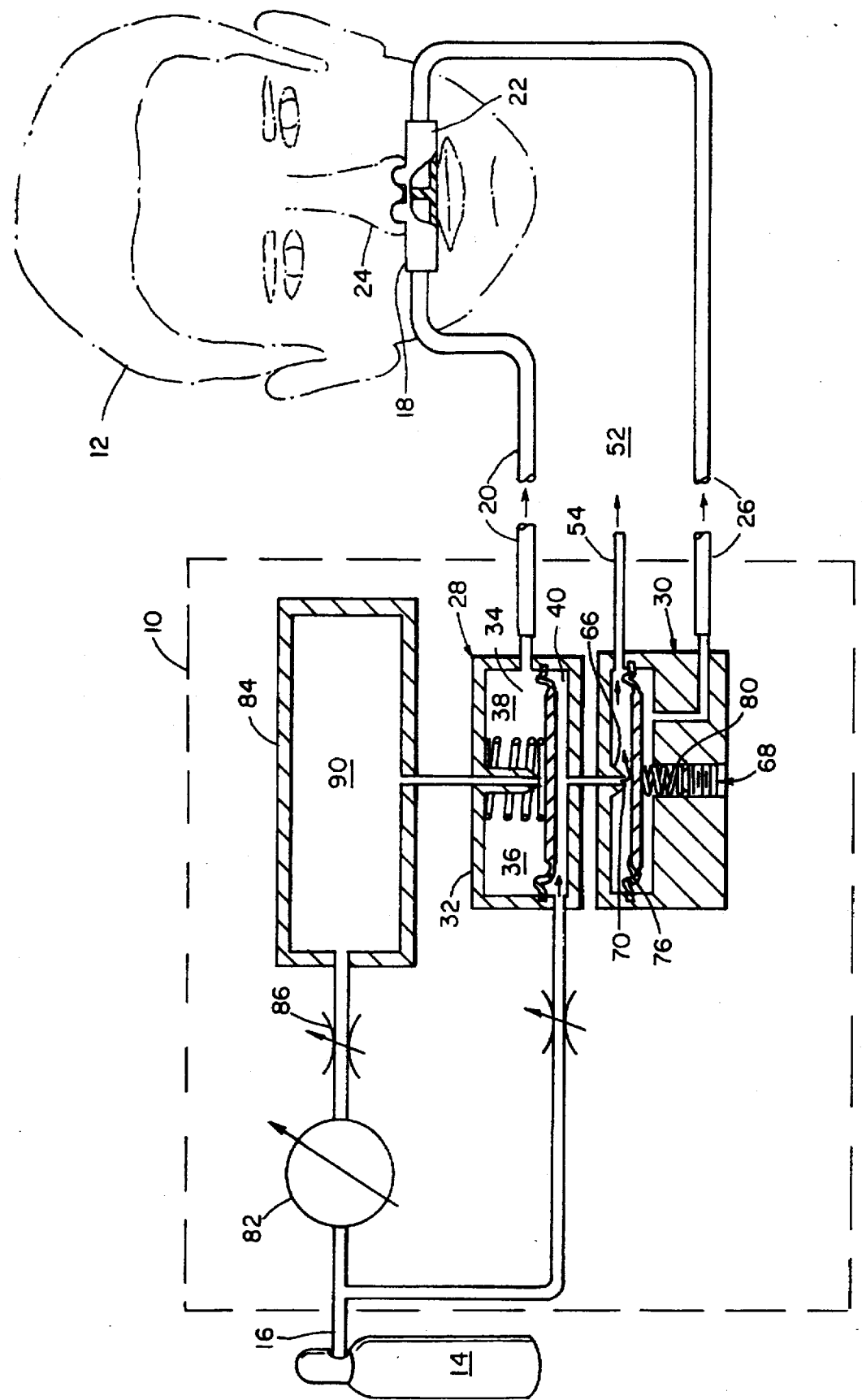
FIG. 2 is partially a schematic view and partially an elevational side view in cross-section of the first exemplary embodiment of the pneumatically-operated gas demand apparatus of the present invention shown coupled between and in fluid communication with the single source of pressurized gas and the recipient with the supply valve in a flow-supplying position and the sensing valve in a flow-causing position as a result of the recipient inhaling.
Figure 3:
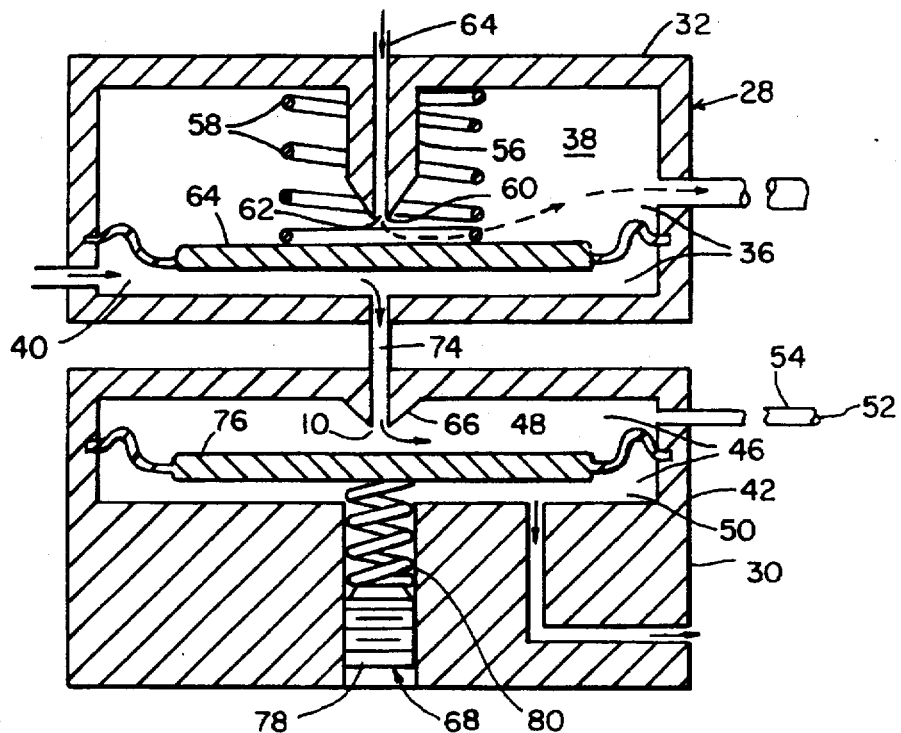
FIG. 3 is an enlarged elevational side view in cross-section of the supply valve in the flow-supplying position and the sensing valve the flow-causing position as shown in FIG. 2.

As generally introduced in FIGS. 1–3, a pneumatically-operated gas demand apparatus 10 is coupled in interruptible fluid communication between a recipient 12 and a source 14 of pressurized oxygen. Conventional tubing 16 interconnects pneumatically-operated gas demand apparatus 10 to source 14 and a partitioned, nasal cannula assembly 18 interconnects pneumatically-operated gas demand apparatus 10 and recipient 12. A dual-lumen, nasal cannula assembly (not shown) can also be employed and is well known in the art and no additional explanation thereof is deemed necessary to practice the present invention. A first lumen 20 of dual-lumen, nasal cannula assembly 18 is connected between pneumatically-operated gas demand apparatus 10 and a cannula 22 to conduct oxygen (as shown by dashed arrows in FIG. 2) to a nose 22 of recipient 12. A second lumen 4 is connected between pneumatically-operated gas demand apparatus 10 and cannula 22 to act as a conduit so that inhalation pressure and exhalation pressure (as shown by solid double-line arrows in FIGS. 1 and 2) from recipient 12 can be conveyed to pneumatically-operated gas demand apparatus 10. As a result, pneumatically-operated gas demand apparatus 10 is adapted for controlling delivery of gaseous oxygen to recipient 12 as recipient 12 inhales and exhales.

Again, with reference to FIGS. 1 and 2, pneumatically-operated gas demand apparatus 10 comprises a supply valve 28 and a sensing valve 30. Supply valve 28 includes a supply valve housing 32 and a flexible first diaphragm member 34. Supply valve housing 32 defines a first interior chamber 36 which is formed therein. Flexible first diaphragm member 34 is disposed within first interior chamber 36 and is connected to supply valve housing 32 in a manner to divide first interior chamber 36 into a supply chamber region 38 and a control chamber region 40. Supply chamber region 38 is in interruptible fluid communication with and between source 14 of the pressurized oxygen and recipient 12. Throughout the description of the exemplary embodiments, the phrase, "interruptible fluid communication" is used and, by way of example only, "interruptible fluid communication" means that sometimes supply chamber region 38 is in fluid communication with source 14 while at other times supply chamber region 38 is not in fluid communication with source 14. Control chamber region 40 is in continuous fluid communication with source 14 of pressurized oxygen. First diaphragm member 34 is operative to hermetically seal supply chamber region 38 and control chamber region 40 from one another. Additionally, first diaphragm member 34 is operative to move between a flow-blocking position as shown in FIG. 1 and a flow-supplying position as shown in FIG. 2.

Sensing valve 30 includes a sensing valve housing 42 and a flexible second diaphragm member 44. Sensing valve housing 42 defines a second interior chamber 46 which is formed therein. Second diaphragm member 44 is disposed within second interior chamber 46 and is connected to sensing valve housing 42 in a manner to divide second interior chamber 46 into a venting chamber region 48 and a sensing chamber region 50. Venting chamber region 48 is in interruptible fluid communication with and between control chamber region 40 of first interior chamber 36 of supply valve 28 and an ambient air environment 52 through a bleed conduit 54. Sensing chamber region 50 is in continuous fluid communication with recipient 12.

Second diaphragm member 44 is operative to hermetically seal venting chamber region 48 and sensing chamber region 50 from one another. Further, second diaphragm member 44 is responsive when recipient 12 inhales and exhales by moving between a flow-stopping position as shown in FIG. 1 and a flow-causing position as shown by FIG. 2. As best shown in FIG. 3, when recipient 12 inhales, second diaphragm member 44 is in the flow-causing position thereby causing oxygen (represented by the single solid line arrows) to flow from control chamber region 40, through venting chamber region 48 and into ambient air environment 52. In turn, second diaphragm member 44 being in the flow-causing position causes first diaphragm member 34 to be in the flow-supplying position thereby delivering oxygen (represented by dashed arrows) from source 14 of pressurized oxygen to recipient 12. As shown in FIG. 2, when recipient 12 exhales, second diaphragm member 44 is in the flow-stopping position thereby preventing oxygen to flow from control chamber region 40, through venting chamber region 48 and into ambient air environment 52 which, in turn, causes first diaphragm member 34 to be in the flow-blocking position thereby preventing delivery of oxygen to recipient 12.

As best shown in FIG. 3, supply valve 28 includes a supply tube stem 56 and a supply valve spring 58. Supply tube stem 56 is disposed within supply chamber region 38 of supply valve 28 and has a supply seat 60 defining a supply opening 62 into a tube stem conduit 64. Tube stem conduit 64 provides fluid communication into supply chamber region 38. Supply seat 60 is sized and adapted to removably contact a blocking side 64 of first diaphragm member 34 in a fluid-tight relation when supply valve 28 is in the flow-blocking position as shown in FIG. 1. Also, as best shown in FIGS. 2 and 3, supply opening 62 is in a spaced-apart, facially-opposing relationship with blocking side 64 when supply valve 28 is in the flow-supplying position. Supply valve spring 58 is disposed within supply chamber region 38 and surrounding supply tube stem 56. Supply valve spring 58 is operative to yieldably urge first diaphragm member 34 into the flow-supplying position.

As best shown in FIG. 3, sensing valve 30 includes a sensing valve seat member 66 and a sensing valve adjustment assembly 68. Sensing valve seat member 66 is disposed in and extends into venting chamber region 48. Sensing valve seat member 66 has a sensing valve seat 70 which defines a flow opening 72 into a supply valve conduit 74. Supply valve conduit 74 provides fluid communication into venting chamber region 48 of sensing valve 30. Sensing valve seat 70 is sized and adapted to removably contact a stopping side 76 of second diaphragm member 44 in a fluid-tight relation when sensing valve 30 is in the flow-stopping position as shown in FIG. 1. Flow opening 72 is in a spaced-apart, facially-opposing relationship from stopping side 72 when sensing valve 30 is in the flow-causing position as shown in FIGS. 2 and 3.

Sensing valve adjustment assembly 68 includes a set screw 78 and a sensing valve spring 80. Set screw 78, threadably mounted into sensing valve housing 42, extends into sensing chamber region 50 and is accessible exteriorly of sensing valve housing 42. Sensing valve spring 80 is disposed within sensing chamber region 50 and in contact with and between set screw 78 and second diaphragm member 44. Sensing valve spring 80 imparts a yieldable tension force "F", shown in FIG. 1, to second diaphragm member 44 against sensing valve seat 70 to resiliently bias second diaphragm member 44 into the flow-stopping position. As commonly known in the art, turning set screw 78 in a first direction "$d_1$" increases tension force "F" and turning set screw 78 in a second direction "$d_2$" opposite the first direction "$d_1$" decreases the tension force "F".

Again referring to FIGS. 1 and 2, pneumatically-operated gas demand apparatus 10 includes a regulator mechanism 82 (drawn symbolically), a bolus chamber structure 84, a supply orifice element 86 (drawn symbolically) and a pilot orifice element 88 (drawn symbolically). For the first exemplary embodiment of the of the present invention, regulator mechanism 82 is a conventional regulator. Regulator mechanism 82 is disposed between and in interruptible fluid communication with source 14 of pressurized oxygen and supply chamber region 38 of supply valve 28. Bolus chamber structure 84 defines a bolus chamber 90 therein and is disposed between and in fluid communication with regulator mechanism 82 and supply chamber region 38 of supply valve 28. Supply orifice element 86 is disposed between regulator mechanism 82 and bolus chamber structure 84. Pilot orifice element 88 is disposed between source 14 of the pressurized oxygen and control chamber region 40 of supply valve 28. By way of example and not limitation, pilot orifice element 88 and supply orifice element 86, as reflected by the symbolic drawings, are of an adjustable, variable orifice type which are commonly known in the art.

Figure 4:
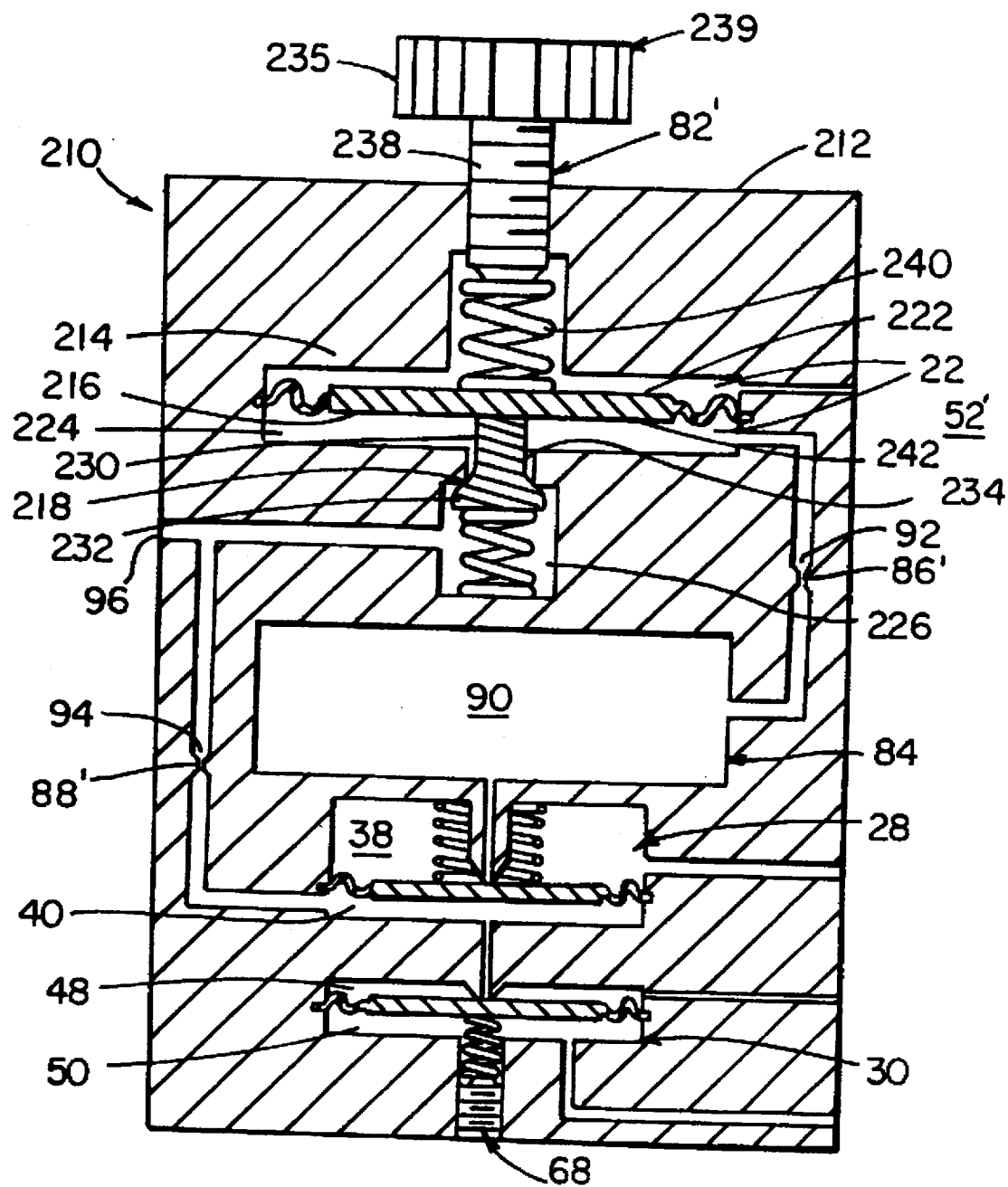
FIG. 4 is an elevational side view in cross-section of a second exemplary embodiment of the pneumatically-operated gas demand apparatus of the present invention integrating the supply valve, the sensing valve and a regulator mechanism into a unitary construction with a valve assembly of the regulator mechanism in a closed condition.
Figure 5:
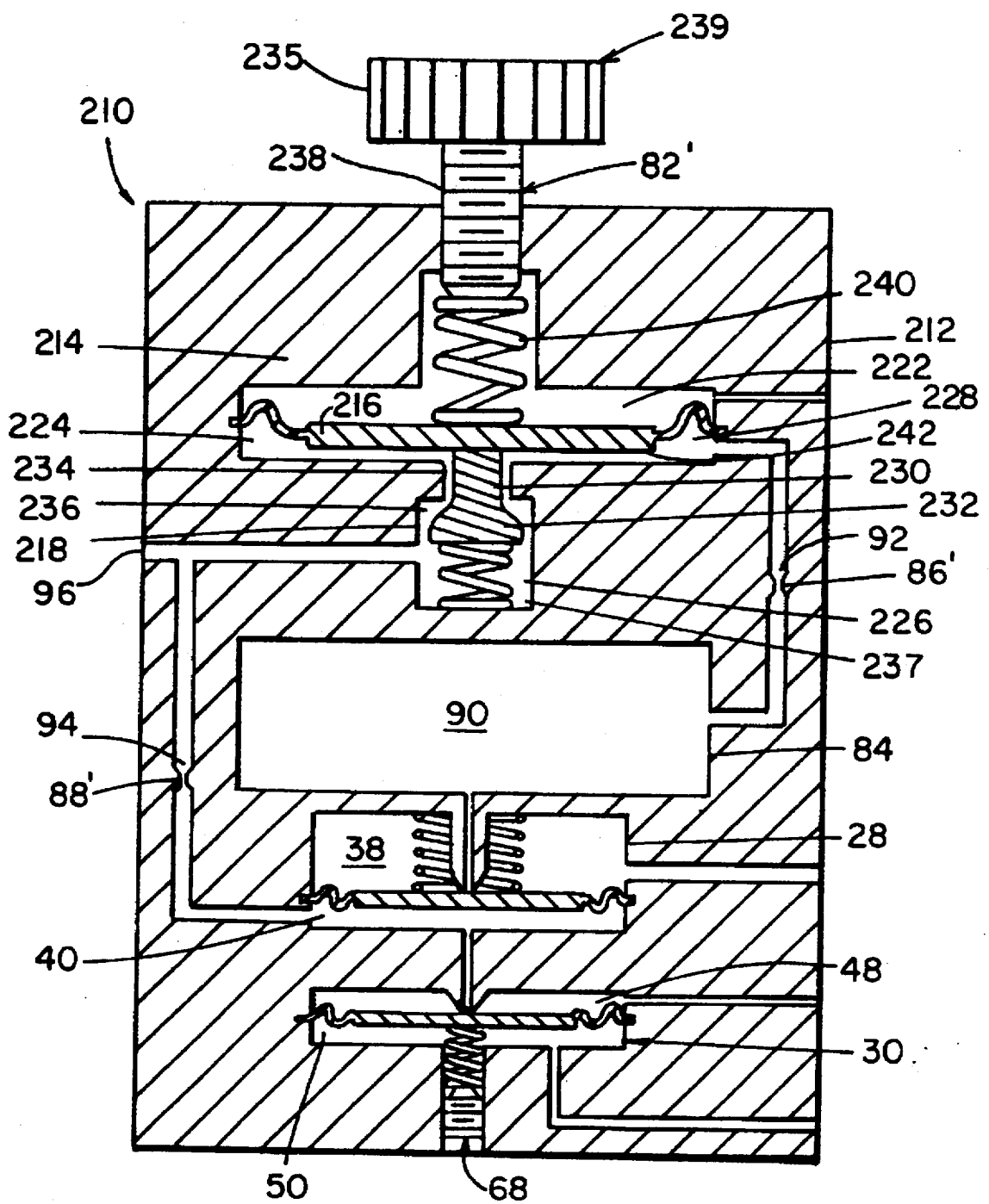
FIG. 5 is an elevational side view in cross-section of the second exemplary embodiment of the pneumatically-operated gas demand apparatus of the present invention of FIG. 4 with the valve assembly of the regulator mechanism in an opened condition.

A second exemplary embodiment of a pneumatically-operated gas demand apparatus 210 of the present invention is introduced in FIGS. 4 and 5. Pneumatically-operated gas demand apparatus 210 of the present invention is functionally similar than the first exemplary embodiment of pneumatically-operated oxygen apparatus 10 of the present invention but includes structural modifications as discussed below. Generally, a skilled artisan would appreciate that pneumatically-operated gas demand apparatus 210 integrates the components referred to hereinabove into a unitary construction. The skilled artisan would further appreciate that pneumatically-operated gas demand apparatus 210 employs a single housing 212 which, in essence, can be subdivided into the various housings, structures, interior chambers and chamber regions of the components described above. Therefore, no further discussion of these components is deemed necessary except as hereinafter described which structurally distinguishes the first and second exemplary embodiments from one another.

With reference to FIGS. 4 and 5, a supply orifice element 86' has a supply orifice 92 which is formed therethrough. Supply orifice 92 is fixed in size and provides fluid communication between a regulator mechanism 82' and bolus chamber 90. A pilot orifice element 88' has a pilot orifice 94 which is formed therethrough. Pilot orifice 94 is also fixed in sized and provides fluid communication with and between source 14 of pressurized oxygen and control chamber region 40 of supply valve 28 through a single inlet 96.

For the second exemplary embodiment of the pneumatically-operated gas demand apparatus 210 of the present invention, regulator mechanism 82' is employed therewith. Regulator mechanism 82' includes a regulator housing 214, a flexible regulator diaphragm 216 and a valve assembly 218. Regulator housing 214 defines a regulator chamber 220 formed therein. Regulator diaphragm 216 is disposed within regulator chamber 220 and is connected to regulator housing 214 in a manner to divide regulator chamber 220 into a vented regulator chamber region 222 and a supply regulator chamber region 224. Vented regulator chamber region 222 is in continuous fluid communication with ambient air environment 52. Supply regulator chamber region 224 is in interruptible fluid communication between source 14 of pressurized oxygen and supply chamber region 38 of supply valve 28. Regulator diaphragm 216 is operative to hermetically seal vented regulator chamber region 222 and supply regulator chamber region 224 from one another.

Valve assembly 218 is operably connected to regulator diaphragm 216 and is disposed within supply regulator chamber region 224. Valve assembly 218 is operative between a closed condition (shown in FIG. 4) and an opened condition (shown in FIG. 5). In the closed condition, an upstream portion 226 of supply regulator chamber region 224 is isolated from fluid communication with a downstream portion 228 of supply regulator chamber region 224. In the opened condition, upstream portion 226 of supply regulator chamber region 224 is in fluid communication with downstream portion 228 of supply regulator chamber region 224. Valve assembly 218 is resiliently and yieldably biased against regulator diaphragm 216 in the closed condition while simultaneously therewith regulator diaphragm 216 is resiliently and yieldably biased against valve assembly 218 in the opened condition. Now, when a gas pressure reaches a threshold gas pressure amount in downstream portion 228 of supply regulator chamber region 224, valve assembly 218 is in the closed condition. And, when the gas pressure is less than the threshold gas pressure amount, valve assembly 218 is in the opened condition so that oxygen can flow from upstream portion 226, through downstream portion 228 and to supply valve 28.

Valve assembly 218 includes a poppet valve stem 230 which has a poppet valve head 232. As best shown in FIG. 5, poppet valve stem 230 is slidably received by a poppet valve conduit 234 having a poppet valve seat 236. Poppet valve seat 236 is sized and adapted to removably receive poppet valve head 232 in a matable, fluid-tight relationship when valve assembly 218 is in the closed condition as shown in FIG. 4. Valve assembly 218 also includes an offset spring 237 which is disposed within upstream portion 226 of supply regulator chamber region 224 and against poppet valve head 232. Offset spring 237 is operative to yieldably urge valve assembly 218 in the closed condition.

Regulator mechanism 82' also has a regulator adjustment assembly 239 with an adjustment screw 238 and a set point spring 240. Adjustment screw 238 is threadably mounted into regulator housing 214 and is accessible exteriorly of regulator housing 214. Adjustment screw 238 also extends into vented regulator chamber region 222. Set point spring 240 is disposed within vented regulator chamber region 222 and in contact with and between adjustment screw 238 and regulator diaphragm 216. As is commonly known in the art, advancing adjustment screw 238 into regulator housing 214 by a turning knob 235 increases a threshold gas pressure amount permitted into downstream portion 228 of supply regulator chamber region 224 from upstream portion 226 of supply regulator chamber region 224 and, correspondingly, retracting adjustment screw 238 by turning knob 235 in an opposite direction decreases the threshold gas pressure amount permitted into downstream portion 228 of supply regulator chamber region 224 from upstream portion 226 of supply regulator chamber region 224. Thus, combined forces of the threshold gas pressure amount acting on a regulating side 242 of regulating diaphragm 216 and offset spring 237 overcome a spring force exerted by set point spring 240 to move valve assembly 218 into the closed condition.

Figure 6:
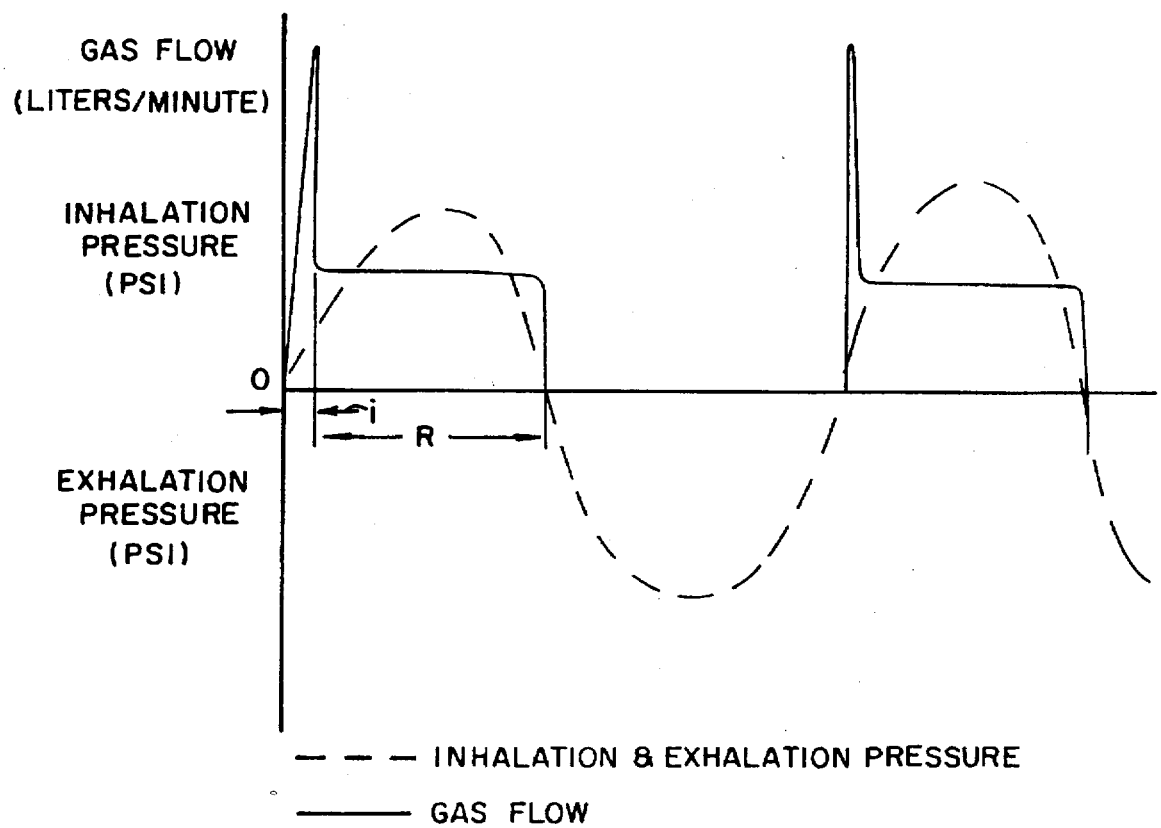
FIG. 6 is a chart illustrating graphically a flow-rate of the gas being delivered to the recipient by the pneumatically-operated gas demand apparatus of the present invention and superimposed onto a sign wave reflecting an inhalation pressure and exhalation pressure of the recipient throughout the recipient's breathing cycle.

Therefore, the oxygen contained in bolus chamber 90 is also under the threshold amount of gas pressure. Now, when recipient inhales, the pneumatically-operated gas demand apparatus of the present invention delivers a high-flow pulse of oxygen to the recipient/patient upon commencement of the recipient's inhalation phase of the breathing cycle. Once the threshold pressure drops thereafter, valve assembly 218 opens and a continuous flow of oxygen is delivered to the recipient throughout the remaining portion of the inhalation phase. FIG. 6 illustrates a flow-rate of the gas, i.e. oxygen, being delivered to the recipient by the pneumatically-operated gas demand apparatus of the present invention and superimposed onto a dashed sign wave which reflects an inhalation pressure and exhalation pressure of the recipient throughout the recipient's breathing cycle. Note the high-flow pulse of oxygen flowing during an initiation period "i" of the inhalation phase of the breathing cycle and the continuous, lower flow of oxygen flowing during a remaining period "r" of the inhalation phase.

One of ordinary skill in the art would appreciate the relationship among regulator mechanism 82 (or 82'), supply orifice element 86 (or 86'), bolus chamber structure 84 defining bolus chamber 90 and supply valve 28. Oxygen is conveyed from regulator mechanism 82 (or 82') into bolus chamber 90 through supply orifice element 86 (or 86'). As with any conventional regulator, regulator mechanism 82 (or 82') is pre-set to control pressure of the oxygen into pneumatically-operated gas demand apparatus of the present invention. Thus, when supply valve 28 is in the flow-blocking position, oxygen flows into bolus chamber 90 only until the pre-set control pressure is achieved. When the oxygen discontinues flowing, bolus chamber 90 is charged with oxygen at the pre-set control pressure of regulator mechanism 82 (or 82'). When supply valve 28 moves to the flow-supplying position, a high flow pulse of oxygen at a high flow rate (indicated by initiation period "i" in FIG. 6), is, in essence, injected to nose 24 of recipient 12 in a brief burst. This pulse of oxygen, in part, displaces a portion of exhaled air extant in the recipient's respiratory passageway at the ending portion of the exhalation phase of the recipient's breathing cycle and, in part, enriches the remaining portion of air therein with oxygen. Upon inhalation, recipient 12 can now ingest oxygen-enriched air from within the recipient's respiratory passageway rather than oxygen-depleted air remaining in the respiratory passageway from the prior expiration.

An oxygen pressure "blow down" occurs in bolus chamber 90 when supply valve 28 moves to the flow-supplying position. With the oxygen "blow down" pressure below the pre-set control pressure, regulator 82 (or 82') activates to convey oxygen at a pre-set pressure through the pneumatically-operated gas demand apparatus of the present invention in a steady state flow during the remaining period "r" of inhalation phase (illustrated by remaining period "r" in FIG. 6). This steady state flow is generally constant throughout remaining period "r" and is less that peak oxygen flow during initiation period "i". This steady state flow is controlled by regulator mechanism 82 (and 82') and the size of supply orifice 92.

Interestingly, the amount of oxygen injected into nose 24 of the recipient 12 is governed by the pre-set pressure of regulator 82 (or 82'). By way of example only and not limitation, the regulator mechanism 82 (or 82') is pre-set at its full-opened state to deliver a maximum amount of oxygen to bolus chamber 90 for which it was designed. If one-half of the amount of oxygen is later prescribed for injection into recipient 12, then regulator mechanism 82 (or 82') is adjusted so that the pre-set is at one-half of its full-opened state.

Figure 7:
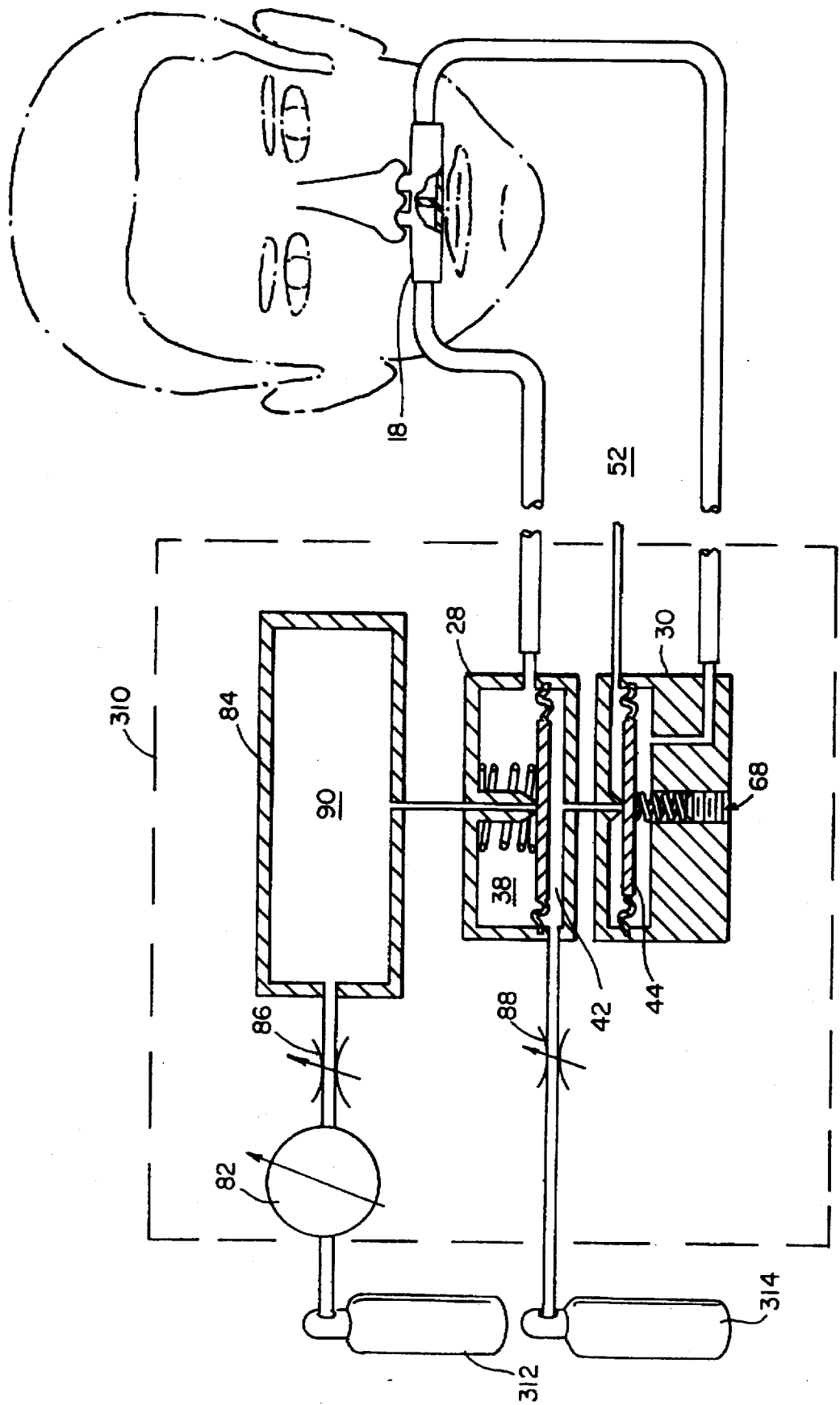
FIG. 7 is partially a schematic view and partially an elevational side view in cross-section of a third exemplary embodiment of the pneumatically-operated gas demand apparatus of the present invention shown coupled between and in fluid communication with two sources of different pressurized gases and a recipient with the supply valve in the flow-blocking position and the sensing valve in the flow-stopping position as a result of the recipient exhaling.
Figure 8:
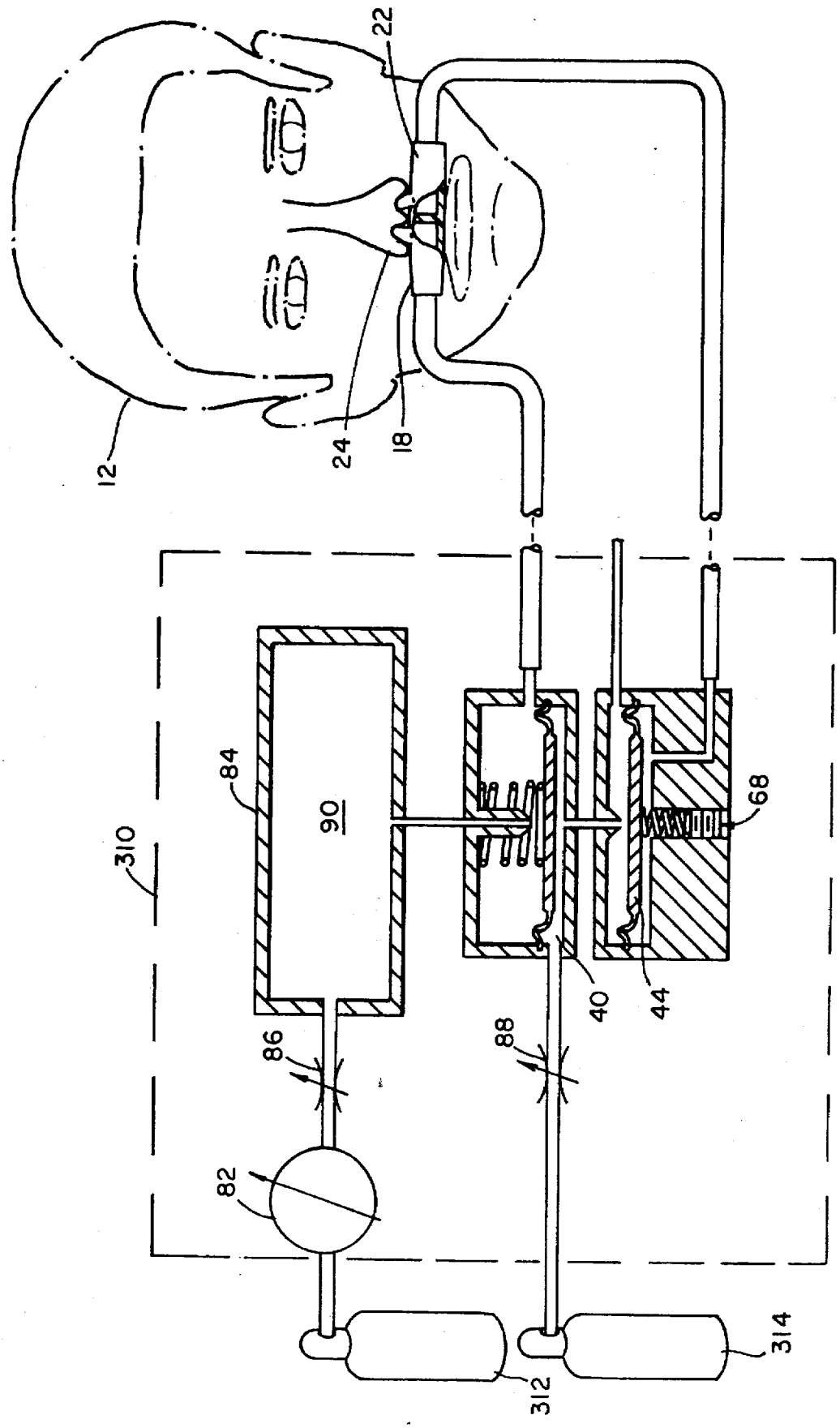
FIG. 8 is partially a schematic view and partially an elevational side view in cross-section of the third exemplary embodiment of the pneumatically-operated gas demand apparatus of the present invention shown coupled between and in fluid communication with the two sources of different pressurized gases and the recipient with the supply valve in the flow-supplying position and the sensing valve in the flow-causing position as a result of the recipient inhaling one while the other gas vents to ambient air environment.

FIGS. 7 and 8 depict a third exemplary embodiment of a pneumatically-operated gas demand apparatus 310 of the present invention. Although structurally similar to the first and second exemplary embodiments of the pneumatically-operated oxygen demand apparatuses of the present invention, the pneumatically-operated gas demand apparatus 310 delivers a first gas from a first gas source 312 and operates on a second gas supplied by a second gas source 314. Obviously, first gas source 312 is different from second gas source 314. It is preferred that the first gas and the second gas are different from one another although the first gas and the second gas can be the same, if desired. It is preferred that the first gas and the second gas are selected from different ones of a group of gases including oxygen, nitrous oxide, air or any other kind of gas. However, it is possible that the first and second gases are selected from the same group of gases, if desired.

In FIGS. 7 and 8, supply chamber region 38 of supply valve 28 is in interruptible fluid communication with and between first source 312 of the first gas and the recipient. Control chamber region 40 of supply valve 28 is in continuous fluid communication with second source 314 of the pressurized second gas. As shown in FIG. 8, when recipient 12 inhales, second diaphragm member 44 of sensing valve 30 is in the flow-causing position thereby causing the second gas to flow from control chamber region 40, through venting chamber region 48 and into ambient air environment 52. This, in turn, causes first diaphragm member 34 to be in the flow-supplying position thereby delivering the first gas from the first source of pressurized first gas to the recipient. In FIG. 7, when the recipient exhales, second diaphragm member 44 is in the flow-stopping position thereby preventing the second gas to flow from control chamber region 40, through venting chamber region 48 and into ambient air environment 52. This, in turn, causes first diaphragm member 34 to be in the flow-blocking position thereby preventing delivery of the first gas to the recipient.

This third exemplary embodiment of the pneumatically-operated gas demand apparatus 310 is particularly useful to prevent wastage of the first gas. For example, oxygen is considered expensive and compressed air is considered inexpensive relative to the cost of oxygen. With oxygen used as the first gas, no oxygen is dissipated to the ambient air environment and all of the oxygen is delivered to the patient. With compressed air as the second gas, the inexpensive compressed air is now dissipated to the ambient air environment.

Figure 9:
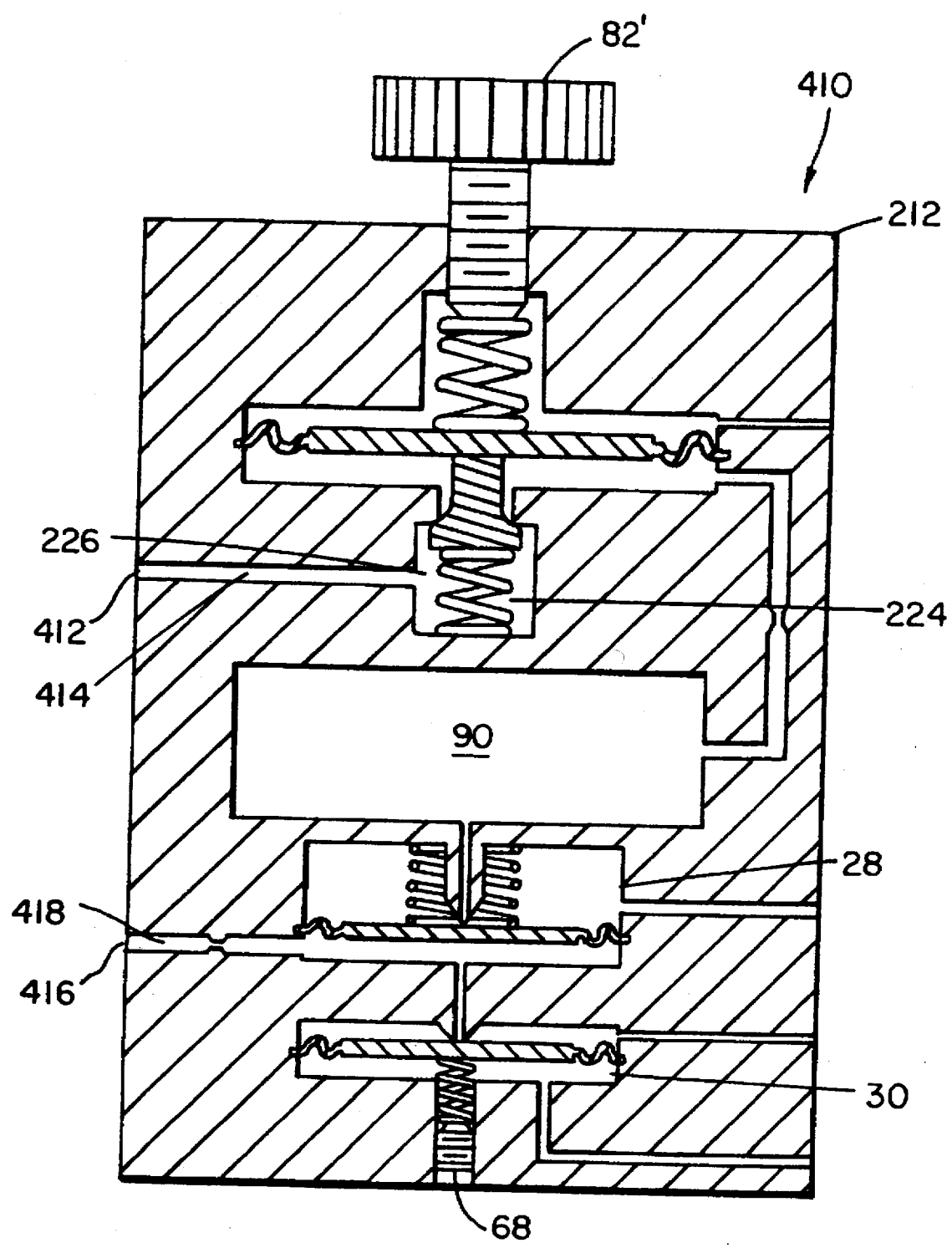
FIG. 9 is an elevational side view in cross-section of a fourth exemplary embodiment of the pneumatically-operated gas demand apparatus of the present invention integrating the supply valve, the sensing valve and the regulator mechanism into a unitary construction with a valve assembly of the regulator mechanism in a closed condition and with the supply valve and the sensing valve having independent inlets for receiving respective ones of the two different gases from independent sources.

A fourth exemplary embodiment of a pneumatically-operated gas demand apparatus 410 is introduced in FIG. 9 and is a unitary construction of the third exemplary embodiment of the pneumatically-operated gas demand apparatus 310. Pneumatically-operated gas demand apparatus 410 has a first gas inlet 412 with a first gas conduit 414 leading into upstream portion 226 of supply regulator chamber region 224. First gas inlet 412 is adapted to connect to the first gas source of the pressurized first gas. Pneumatically-operated gas demand apparatus 410 has a second gas inlet 416 with a second gas conduit 418 leading into control chamber region 224 of supply valve 28. Second gas inlet 416 is adapted to connect to the second gas source of the pressurized second gas.

Figure 10:
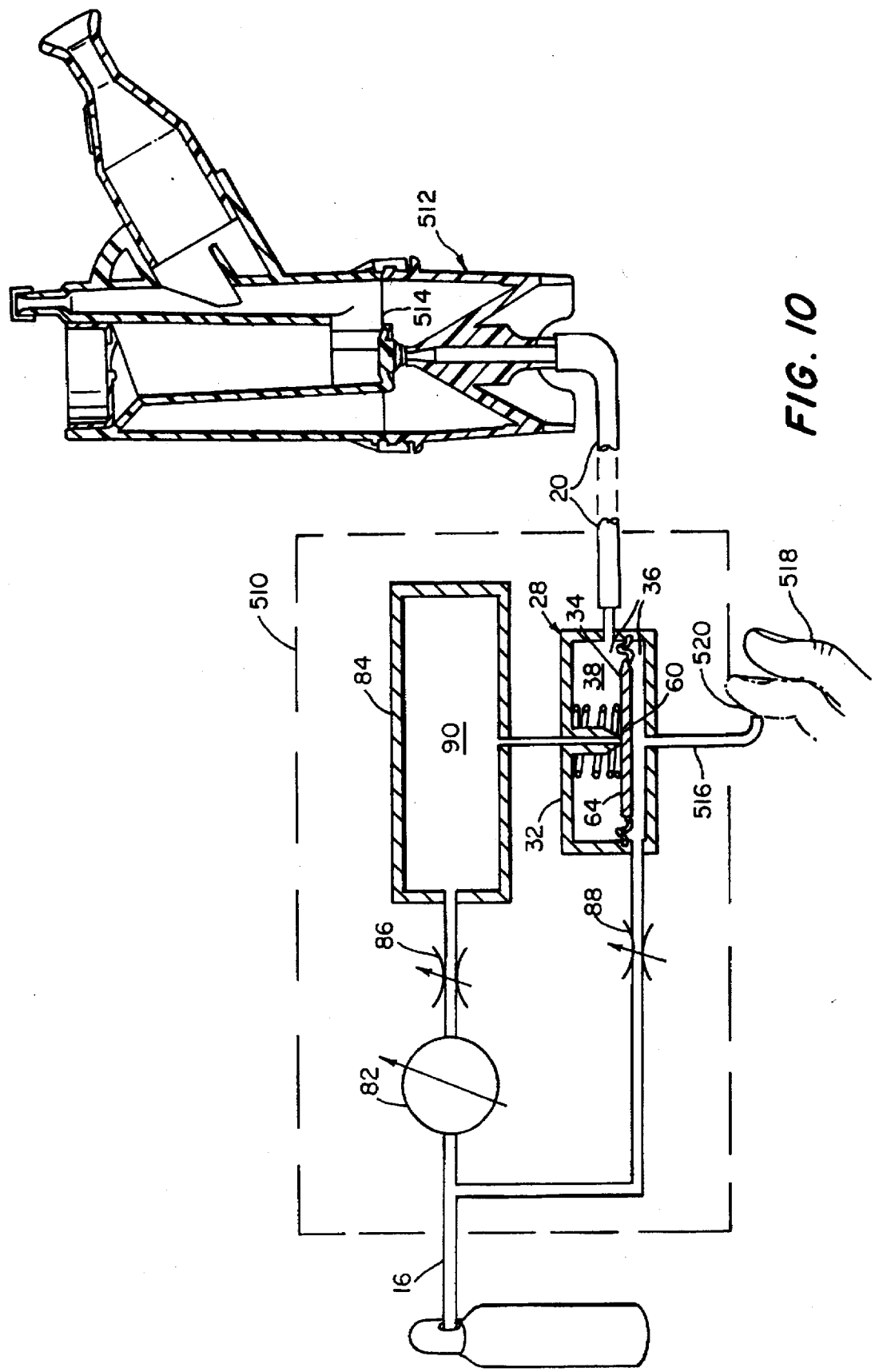
FIG. 10 is a partial schematic view and a partial cross-sectional view of a fifth exemplary embodiment of the present invention which is an intermittent gas delivery device used in combination with a conventional nebulizer.

A skilled artisan would appreciate that regulator mechanism 82 (or 82'), supply orifice element 86 (or 86'), bolus chamber structure 84 and supply valve 28 can be combined in a manner described hereinabove to construct an intermittent gas delivery device 510 as generally introduced in FIG. 10. Intermittent gas delivery device 510 could be utilized, for example, with a nebulizer 512 such as the one described in a patent application filed on even date herewith by inventors James Chua and Peter W. Salter. Other nebulizers are commonly known in the art and can be employed with the present invention if equipped with an inhalation sensing structure or supplemental sensing apparatus. With intermittent gas delivery device 510 connected in fluid communication between gas source 14 of pressurized gas, such as air or oxygen, and nebulizer 512, intermittent gas delivery device 510 generates a fine-mist plume 514 of a medicament-containing aerosol by first permitting the pressurized gas into nebulizer 512. Initially, a high flow pulse of the pressurized gas generates this fine-mist plume and subsequently a steady state flow of the gas delivered to nebulizer 512 continues to generate and deliver this fine-mist plume to the patient. The high flow pulse and subsequent steady flow sequentially occurs by the implementation of a sense tube 516. A finger 518 of recipient 12 being placed over a sense tube inlet 520 causes supply valve to be in the flow-blocking position. Removing finger 518 from sense tube inlet 520 causes supply valve 28 to move to the flow-supplying position. One of ordinary skill in the art would appreciate that other methods such as mechanically triggering supply valve 28 during a selected interval of time within each breathing cycle could be utilized in lieu thereof.

The pneumatically-operated gas demand apparatus of the present invention can minimize wastage of oxygen, if desired. The pneumatically-operated gas demand apparatus delivers a high-flow pulse of oxygen to the recipient/patient during an initiation period of the recipient/patient's inhalation phase of the breathing cycle. This high-flow pulse of oxygen causes oxygen enrichment of the exhaled air remaining in a nasal and other portions of the respiratory passageway from the prior exhalation phase of the breathing cycle. With this enriched exhaled air now becoming the first air to be inhaled into the recipient's lungs, more therapeutically valuable oxygen can be utilized by the recipient. Thereafter, a continuous flow of oxygen is delivered to the recipient throughout the remaining period of inhalation phase of the breathing cycle. As described, the pneumatically-operated gas demand apparatus can be fabricated from readily available components or can be integrated into a unitary construction. In either regard, the pneumatically-operated gas demand apparatus is simple in design and compact.

Accordingly, the present invention has been described with some degree of particularity directed to the exemplary embodiments of the present invention. It should be appreciated, though, that the present invention is defined by the following claims construed in light of the prior art so that modifications or changes may be made to the exemplary embodiments of the present invention without departing from the inventive concepts contained herein.

I claim:

1. In combination with a nebulizer for producing a medicament-containing aerosol and a source of pressurized gas, an intermittent gas delivery device disposed between and in intermittent fluid communication with the nebulizer and the source of pressurized gas, comprising:

(a) a regulator mechanism in continuous fluid communication with and disposed downstream of the source of pressurized gas;

(b) a bolus chamber structure defining a bolus chamber therein and disposed downstream of and in fluid communication with said regulator mechanism;

(c) a supply orifice element having a supply orifice formed therethrough, said supply orifice element disposed between said regulator mechanism and said bolus chamber, said supply orifice providing fluid communication between said regulator mechanism and said bolus chamber; and (d) a supply valve in downstream fluid communication with said supply orifice and operative to move between a flow-blocking position whereby the pressurized gas is prevented from flowing from the source to the nebulizer and a flow-supplying position whereby the pressurized gas flows from the source to the nebulizer such that a high flow pulse of pressurized gas first generates a fine-mist plume of the medicament-containing aerosol in the nebulizer and subsequently a steady state flow of pressurized gas continues to produce the fine-mist plume of the medicament-containing aerosol in the nebulizer until said supply valves moves to the flow-blocking position.

2. An intermittent gas delivery device according to claim 1 including a sensing valve operably connected to said supply valve and the source of pressurized gas to cause said supply valve to move between the flow-causing and the flow-blocking positions.

3. An intermittent gas delivery device according to claim 1 including a sense tube connected in fluid communication with said supply valve and having a sense tube inlet thereinto, said sense tube operative with a finger of the recipient to be placed over a sense tube inlet 518 to cause said supply valve to be in the flow-blocking position and to be removed from said sense tube inlet to cause said supply valve to move to the flow-supplying position.

4. A pneumatically-operated gas demand apparatus according to claim 3 wherein said regulator mechanism includes a regulator housing, a flexible regulator diaphragm and a valve assembly, said regulator housing defining a regulator chamber therein, said regulator diaphragm disposed within said regulator chamber and connected to said regulator housing in a manner to divide said regulator chamber into a vented regulator chamber region in continuous fluid communication with the ambient air environment and a supply regulator chamber region in interruptible fluid communication between the first source of pressurized first gas and said supply chamber region of said supply valve, said regulator diaphragm operative to hermetically seal said vented regulator chamber region and said supply regulator chamber region from one another, said valve assembly operably connected to said regulator diaphragm and disposed within said supply regulator chamber region, said valve assembly operative between a closed condition whereby an upstream portion of said supply regulator region is in fluid isolation with a downstream portion of said supply regulator region and an opened condition whereby said upstream portion of said supply regulator region is in fluid communication with said downstream portion of said supply regulator region, said valve assembly resiliently and yieldably biased against said regulator diaphragm in the closed condition, said regulator diaphragm resiliently and yieldably biased against said valve assembly in the opened condition whereby when a first gas pressure of the first gas reaches a threshold gas pressure amount in said downstream portion of said supply regulator region, said valve assembly is in the closed condition and when said first gas pressure is less than said threshold gas pressure amount, said valve assembly is in the opened condition.

5. A pneumatically-operated gas demand apparatus coupled in interruptible fluid communication between a recipient and a first source of a pressurized first gas and adapted for controlling delivery of the first gas to the recipient as the recipient inhales and exhales, comprising:

(a) a supply valve including a supply valve housing defining a first interior chamber formed therein and a flexible first diaphragm member disposed within said first interior chamber and connected to said supply valve housing in a manner to divide said first interior chamber into a supply chamber region and a control chamber region, said supply chamber region being in interruptible fluid communication with and between the first source of the first gas and the recipient, said control chamber region being in continuous fluid communication with a second source of a pressurized second gas, said first diaphragm member operative to hermetically seal said supply chamber region and said control chamber region from one another and to move between a flow-blocking position and a flow-supplying position;

(b) a sensing valve including a sensing valve housing defining a second interior chamber formed therein and a flexible second diaphragm member disposed within said second interior chamber and connected to said sensing valve housing in a manner to divide said second interior chamber into a venting chamber region and a sensing chamber region, said venting chamber region being in interruptible fluid communication with and between said control chamber region of said first interior chamber of said supply valve and an ambient air environment, said sensing chamber region being in continuous fluid communication with the recipient, said second diaphragm member operative to hermetically seal said venting chamber region and said sensing chamber region from one another and responsive when the recipient inhales and exhales to move between a flow-stopping position and a flow-causing position whereby, when the recipient inhales, said second diaphragm member is in the flow-causing position thereby causing the second gas to flow from said control chamber region, through said venting chamber region and into the ambient air environment which, in turn, causes said first diaphragm member to be in the flow-supplying position thereby delivering the first gas from the first source of pressurized first gas to the recipient and, when the recipient exhales, said second diaphragm member is in the flow-stopping position thereby preventing the second gas to flow from said control chamber region, through said venting chamber region and into the ambient air environment which, in turn, causes said first diaphragm member to be in the flow-blocking position thereby preventing delivery of the first gas to the recipient;

(c) a pilot orifice element having a pilot orifice extending therethrough, said pilot orifice element disposed between the second source of pressurized second gas and said control chamber region of said supply valve, said pilot orifice providing fluid communication between the second source of pressurized second gas and said control chamber region;

(d) a regulator mechanism disposed between and in interruptible fluid communication with the first source of the first gas and said supply chamber region of said supply valve; and (e) a bolus chamber structure defining a bolus chamber therein and disposed between and in fluid communication with said regulator mechanism and said supply chamber region of said supply valve.

6. A pneumatically-operated gas demand apparatus according to claim 5 wherein the first gas and the second gas are the same.

7. A pneumatically-operated gas demand apparatus according to claim 6 wherein the first gas and the second gas are selected from a group of gases consisting of oxygen, nitrous oxide and air.

8. A pneumatically-operated gas demand apparatus according to claim 5 wherein the first gas and the second gas are different from each other.

9. A pneumatically-operated gas demand apparatus according to claim 8 wherein the first gas and the second gas are selected from different ones of a group consisting of oxygen, nitrous oxide and air.

10. A pneumatically-operated gas demand apparatus according to claim 5 including a supply orifice element having a supply orifice formed therethrough, said supply orifice element disposed between said regulator mechanism and said bolus chamber, said supply orifice providing fluid communication between said regulator mechanism and said bolus chamber.

11. A pneumatically-operated gas demand apparatus coupled in interruptible fluid communication between a recipient and a first source of a pressurized first gas and adapted for controlling delivery of the first gas to the recipient as the recipient inhales and exhales, comprising:

(a) a supply valve including a supply valve housing defining a first interior chamber formed therein and a flexible first diaphragm member disposed within said first interior chamber and connected to said supply valve housing in a manner to divide said first interior chamber into a supply chamber region and a control chamber region, said supply chamber region being in interruptible fluid communication with and between the first source of the first gas and the recipient, said control chamber region being in continuous fluid communication with a second source of a pressurized second gas, said first diaphragm member operative to hermetically seal said supply chamber region and said control chamber region from one another and to move between a flow-blocking position and a flow-supplying position;

(b) a sensing valve including a sensing valve housing defining a second interior chamber formed therein and a flexible second diaphragm member disposed within said second interior chamber and connected to said sensing valve housing in a manner to divide said second interior chamber into a venting chamber region and a sensing chamber region, said venting chamber region being in interruptible fluid communication with and between said control chamber region of said first interior chamber of said supply valve and an ambient air environment, said sensing chamber region being in continuous fluid communication with the recipient, said second diaphragm member operative to hermetically seal said venting chamber region and said sensing chamber region from one another and responsive when the recipient inhales and exhales to move between a flow-stopping position and a flow-causing position whereby, when the recipient inhales, said second diaphragm member is in the flow-causing position thereby causing the second gas to flow from said control chamber region, through said venting chamber region and into the ambient air environment which, in turn, causes said first diaphragm member to be in the flow-supplying position thereby delivering the first gas from the first source of pressurized first gas to the recipient and, when the recipient exhales, said second diaphragm member is in the flow-stopping position thereby preventing the second gas to flow from said control chamber region, through said venting chamber region and into the ambient air environment which, in turn, causes said first diaphragm member to be in the flow-blocking position thereby preventing delivery of the first gas to the recipient;

(c) a supply orifice element having a supply orifice formed therethrough, said supply orifice element disposed between said first source of the first gas and said supply chamber region of said supply valve, said supply orifice providing fluid communication between said first source of pressurized first gas and said supply chamber region of said supply valve; and (d) a bolus chamber structure defining a bolus chamber therein and disposed between and in fluid communication with supply orifice element and said supply chamber region of said supply valve.

12. A pneumatically-operated gas demand apparatus coupled in interruptible fluid communication between a recipient and a first source of a pressurized first gas and adapted for controlling delivery of the first gas to the recipient as the recipient inhales and exhales, comprising:

(a) a supply valve including a supply valve housing defining a first interior chamber formed therein and a flexible first diaphragm member disposed within said first interior chamber and connected to said supply valve housing in a manner to divide said first interior chamber into a supply chamber region and a control chamber region, said supply chamber region being in interruptible fluid communication with and between the first source of the first gas and the recipient, said control chamber region being in continuous fluid communication with a second source of a pressurized second gas, said first diaphragm member operative to hermetically seal said supply chamber region and said control chamber region from one another and to move between a flow-blocking position and a flow-supplying position;

(b) a sensing valve including a sensing valve housing defining a second interior chamber formed therein and a flexible second diaphragm member disposed within said second interior chamber and connected to said sensing valve housing in a manner to divide said second interior chamber into a venting chamber region and a sensing chamber region, said venting chamber region being in interruptible fluid communication with and between said control chamber region of said first interior chamber of said supply valve and an ambient air environment, said sensing chamber region being in continuous fluid communication with the recipient, said second diaphragm member operative to hermetically seal said venting chamber region and said sensing chamber region from one another and responsive when the recipient inhales and exhales to move between a flow-stopping position and a flow-causing position whereby, when the recipient inhales, said second diaphragm member is in the flow-causing position thereby causing the second gas to flow from said control chamber region, through said venting chamber region and into the ambient air environment which, in turn, causes said first diaphragm member to be in the flow-supplying position thereby delivering the first gas from the first source of pressurized first gas to the recipient and, when the recipient exhales, said second diaphragm member is in the flow-stopping position thereby preventing the second gas to flow from said control chamber region, through said venting chamber region and into the ambient air environment which, in turn, causes said first diaphragm, member to be in the flow-blocking position thereby preventing delivery of the first gas to the recipient;

(c) a regulator mechanism disposed between and in interruptible fluid communication with the source of pressurized oxygen and said supply chamber region of said supply valve; and (d) a bolus chamber structure defining a bolus chamber therein and disposed between and in fluid communication with said regulator mechanism and said supply chamber region of said supply valve.

13. A pneumatically-operated gas demand apparatus according to claim 12 including a supply orifice element having a supply orifice formed therethrough, said supply orifice element disposed between said regulator mechanism and said bolus chamber, said supply orifice providing fluid communication between said regulator mechanism and said bolus chamber.

* * * * *